US012805823B2

(12) United States Patent
Roser

(10) Patent No.: US 12,805,823 B2
(45) Date of Patent: Nov. 24, 2026

(54) IMAGING WITH SCATTER CORRECTION WITH THE AID OF NOISY SCATTER ESTIMATIONS AND SCATTER INTERPOLATION

(71) Applicant: Siemens Healthineers AG, Forchheim (DE)

(72) Inventor: Philipp Roser, Allston, MA (US)

(73) Assignee: Siemens Healthineers AG, Forchheim (DE)

(*) Notice: Subject to any disclaimer, the term of this patent is extended or adjusted under 35 U.S.C. 154(b) by 0 days.

(21) Appl. No.: 19/252,374

(22) Filed: Jun. 27, 2025

(65) Prior Publication Data

US 2026/0000377 A1 Jan. 1, 2026

(30) Foreign Application Priority Data

Jun. 27, 2024 (DE) ..................... 10 2024 206 001.1

(51) Int. Cl.

| | |
|---|---|
| ***A61B 6/00*** | (2024.01) |
| ***G06T 11/00*** | (2026.01) |
| ***G06T 12/10*** | (2026.01) |
| ***G16H 30/40*** | (2018.01) |

(52) U.S. Cl.

CPC .......... *A61B 6/5282* (2013.01); *A61B 6/5205* (2013.01); *A61B 6/5235* (2013.01); *G06T 12/10* (2026.01); *G16H 30/40* (2018.01); *G06T 2211/441* (2023.08)

(58) Field of Classification Search

CPC ..... A61B 6/4085; A61B 6/4441; A61B 6/483; A61B 6/5205; A61B 6/5235; A61B 6/5241; A61B 6/5282; G01N 23/046; G06T 12/10; G06T 2207/10081; G06T 2207/10116; G06T 2207/20081; G06T 2207/20084; G06T 2211/441; G06T 5/60; G06T 5/70; G16H 30/40

See application file for complete search history.

(56) References Cited

U.S. PATENT DOCUMENTS

| | | | |
|---|---|---|---|
| 2021/0330274 | A1 | 10/2021 | Birkhold |
| 2024/0245378 | A1 | 7/2024 | Roser |

OTHER PUBLICATIONS

Maier, Joscha, et al. "Real-time scatter estimation for medical CT using the deep scatter estimation: method and robustness analysis with respect to different anatomies, dose levels, tube voltages, and data truncation." Medical physics 46.1 (2019): 238-249.

(Continued)

*Primary Examiner* — Michael T Rozanski

(74) *Attorney, Agent, or Firm* — Lempia Summerfield Katz LLC

(57) ABSTRACT

A method for training an algorithm for machine learning for a correction of recordings obtained by an imaging apparatus. A number of output images are recorded. Moreover a smaller number of first, high-quality scattered radiation images are simulated from the output images. A corresponding number of second, low-quality scattered radiation images is further simulated, wherein the simulation is undertaken with a number of photons reduced by at least an order of magnitude. The algorithm is trained with the second, low-quality scattered radiation images as input data and the first, high-quality scattered radiation images as output data.

8 Claims, 7 Drawing Sheets

(56) References Cited

OTHER PUBLICATIONS

Wikipedia: C-arm X-ray machine—pp. 1-3.https://de.wikipedia.org/wiki/C-Bogen_(R%C3%B6ntgenger%C3%A4t).

Wu, Dufan, Kyungsang Kim, and Quanzheng Li. "Computationally efficient deep neural network for computed tomography image reconstruction." Medical physics 46.11 (2019): 4763-4776.

IMAGING WITH SCATTER CORRECTION WITH THE AID OF NOISY SCATTER ESTIMATIONS AND SCATTER INTERPOLATION

CROSS REFERENCE TO RELATED APPLICATIONS

This application claims the benefit of DE 10 2024 206 001.1 filed on Jun. 27, 2024, which is hereby incorporated by reference in its entirety.

FIELD

Embodiments relate to a method for training an algorithm for machine learning for a correction of recordings obtained by an imaging apparatus.

BACKGROUND

Modern imaging methods, for example x-ray-based imaging methods, are employed, inter alia, for diagnostic purposes and for supporting interventions. In such cases structures of the object to be examined with high x-ray absorption may cause a high x-ray contrast. Tools or other devices introduced into the object to be examined or other devices within the object, in a vessel structure of the object for example, may also cause a high x-ray contrast. Objects with high x-ray absorption that cause a high contrast are also referred to as high-contrast objects.

For support of diagnostic purposes it is desirable to a achieve an image quality that is as high as possible. In order to make it possible to trace a device as accurately as possible, in relation to a vessel structure for example, and thus to make possible a guidance of the device that is exact as possible, it is likewise desirable to achieve an image quality that is as high as possible. For example in the context of x-ray-based imaging methods it might possibly be difficult to clearly recognize structures or the device and to clearly distinguish them from other elements of the image, from representations of tissue or bone structures for example or also from the vessel structure. The same applies to the ability to recognize the vessel structure compared to other tissue or the like.

Scattered x-ray photons play an important role in the image quality, both for 2D x-ray projections as well as also for 3D reconstructions, for example of cone beam computed tomography (CBCT). Without suitable compensation scattered rays drastically adversely affect the image quality able to be achieved and lead to striping, cupping (elevation in the center) and smudging artifacts, that may possibly lead to an incorrect diagnosis or treatment. The terms radiation and x-ray radiation are used synonymously here and below. For avoidance of adverse effects on the image quality by scattered radiation, by so-called scattered radiation artifacts, an anti-scatter grid is usually used in front of the detector in today's commercial systems with CBCT capabilities, that physically blocks the x-rays arriving at it. Scattered rays are especially efficiently blocked by anti-scatter grids. This grid also has disadvantageous effects however. It also blocks a part of the non-scattered primary radiation, that may increase the applied dose (because of automatic adjustment). With 2D image quality, a better image quality and a lower dose may be achieved when the anti-scatter grid is removed and there is exclusive reliance on so-called air gap technology. This applies for example for neurovascular interventions in the brain, for example in the treatment of aneurysms or embolic strokes. In order to avoid the use of anti-scatter grids, a specific software solution for scatter compensation in CBCT imaging is desirable.

Recently methods based on what is known as deep learning have been proposed in order to compensate for scatter in the projection area (Maier, J., Eulig, E., Vöth, T., Knaup, M., Kuntz, J., Sawall, S. and Kachelrieβ, M. (2019), Real-time scatter estimation for medical CT using the deep scatter estimation: Method and robustness analysis with respect to different anatomies, dose levels, tube voltages, and data truncation. Med. Phys., 46:238-249. https://doi.org/10.1002/mp.13274). While these methods are extremely fast, their general robustness is questionable because of their dependence on the training data. Because of this dependence it is difficult to cover all possible combinations of x-ray physics, collimation, focal point size and so forth in one combined training cohort. What is more such methods may only be trained with simulated pairs of input and output data, whereby a significant gap arises between simulation and reality.

The de-facto gold standard is the simulation of x-ray physics, either by direct and deterministic solution of the Boltzmann transport equation or by stochastic approximation to the image arising with the aid of Monte-Carlo methods. While these methods deliver highly precise results, their application in the diagnostic and interventional environment is questionable because of their inherent high computational complexity and thus high computation times.

The same applies to so-called empirical methods, that estimate and optimize the x-ray scatter on the basis of an image quality metric in the reconstructed image slices. These methods include many reconstruction steps, that likewise leads to a high computational complexity.

Known from the publication US 2021/0 330 274 A1 is a computer-implemented method for correction of x-ray image data in relation to noise effects. A statistical physical model, that is parameterized with model parameters, is used in order to describe the noise effects.

BRIEF SUMMARY AND DESCRIPTION

The scope of the embodiments is defined solely by the appended claims and is not affected to any degree by the statements within this summary. The present embodiments may obviate one or more of the drawbacks or limitations in the related art. Independent of the grammatical term usage, individuals with male, female or other gender identities are included within the term.

Embodiments provide an improved concept for imaging, for example for x-ray-based imaging, by which a high image quality with reduced computational complexity may be achieved.

A method for training an algorithm for machine learning (especially a neural network) for a correction of recordings obtained by an imaging apparatus is provided. The imaging apparatus may involve an x-ray imaging apparatus for example, in which the recordings are obtained by x-ray radiation. For example, this may involve a CT (computed tomography) device, such as possibly a C-arm device.

In a first step, a plurality of output images with different recording coordinates are recorded by the imaging apparatus, i.e. recordings are obtained. The subsequent image processing starts from these output images. Various recording coordinates of the imaging apparatus are used for the recording of these output images. For example, the recordings are obtained from different angles with regard to the object to be recorded. In this case the angle coordinates form the corresponding recording coordinates. The recording coordinates may however also involve linear coordinates or other coordinates.

In a further step there is a simulation of a number, that is less than the plurality of output images, of first scattered radiation images from the plurality of output images by a scatter model, wherein the simulation is undertaken with a first number of photons and each first scattered radiation image is assigned (at least) one respective recording coordinate. Thus scattered radiation images are obtained by simulation from the previously recorded output images, the quality of which depends on the first number of photons. In this case the same number of scattered radiation images as output images is not obtained or simulated, but a reduced number of first scattered radiation images compared to the plurality of output images. The simulation effort is reduced thereby. If for example 500 projection images or output images are recorded, then for example only ten first scattered radiation images are simulated by the scatter model. The number of scattered radiation images may be fewer by the factor of 2, 3 and so forth, for example by at least an order of magnitude, than the number of the output images. The simulation may be undertaken by a Monte-Carlo method for example or by deterministic computation. Each simulated first scattered radiation image in this case is assigned a respective recording coordinate or a respective set of recording coordinates. For example a simulated first scattered radiation image is assigned a recording angle of a C-arm device as its recording coordinate. From this coordinate the angle of incidence of the radiation onto the object to be examined is produced in the scatter model for example.

In a further step there is a simulation of a same or higher number of second scattered radiation images by the scatter model from the plurality of output images, wherein the simulation is undertaken with a second number of photons reduced by at least an order of magnitude by comparison with the first number. Since the second scattered radiation images are simulated with a reduced number of photons, on the one hand the computing effort for their simulation is reduced and on the other hand also their quality, wherein quality is to be understood as the accuracy and physical correctness. In this sense the first scattered radiation images may thus also be referred to as high-quality or higher-quality, the second scattered radiation images as low-quality or lower-quality. Here and below the terms first scattered radiation images and high-quality scattered radiation images will be used synonymously, likewise the terms second scattered radiation images and low-quality scattered radiation images.

Respective recording coordinates of the second, low-quality scattered radiation images correspond to those of the first, high-quality scattered radiation images. Thus a small number (smaller than the number of the output images) of low-quality scattered radiation images is created by simulation. The number of low-quality scattered radiation images corresponds to that of the high-quality scattered radiation images.

In the last step just as many second, low-quality scattered radiation images as output images may also be simulated. Then, the reduced number of the necessary low-quality scattered radiation images may be taken from this higher number of low-quality scattered radiation images. In this case those low-quality scattered radiation images taken or provided by simulation are those of which the recording coordinates correspond to those of the likewise simulated high-quality scattered radiation images. For example the high-quality and the low-quality scattered radiation images are each simulated for a small number of recording angles.

In an another step, second, low-quality scattered radiation images may also be simulated according to various methods or according to various scatter models. The number of second scattered radiation images would then additionally depend on the number of simulation models used. For example for the use of two different simulation models twice the number of second scattered radiation images would be simulated.

The simulation of the second, low-quality scattered radiation images does not necessarily have to be undertaken directly from the output images, likewise the simulation of the first, high-quality scattered radiation images does not necessarily have to be undertaken directly from the output images. Instead, as will be explained in greater detail below, a 3D image is first of all reconstructed from the output images. In this form of embodiment the second, low-quality scattered radiation images and where necessary also the first, high-quality scattered radiation images will subsequently then be simulated by the scattered radiation model for this 3D image.

The training of the algorithm for machine learning is then undertaken with the second, low-quality scattered radiation images as input data and the first, high-quality scattered radiation images as output data. The algorithm for machine learning may involve a neural network. The term neural network is also to be understood below as being representative of other algorithms for machine learning. The neural network is thus trained with the reduced number of low-quality scattered radiation images and the associated high-quality scattered radiation images. For this the low-quality scattered radiation images in practice form the so-called input layer and the likewise simulated high-quality scattered radiation images form the so-called output layer. The neural network is thus trained on the basis of a reduced number of pairs of simulated low-quality and high-quality scattered radiation images. Thus a reduction in the computing effort may be achieved.

If several simulation models are used for the simulation of the second, low-quality scattered radiation images, several pairs of simulated low-quality and high-quality scattered radiation images may accordingly be used for the training of the neural network. If for example two simulation models are used for simulation of low-quality scattered radiation images, one low-quality radiation image from each of the simulation models may be used for the training of the neural network for each high-quality scattered radiation image. In other words in this example case two different pairs each with different low-quality scattered radiation images would be produced for each high-quality scattered radiation image. The different simulation models in this case may for example have different physically relevant characteristics. In this way the training of the neural network by taking into account the different physically relevant characteristics of the simulation models is further improved.

Alongside the simulation of a few noise-free scattered radiation images of high quality (HQ), a few or a whole stack (corresponding to the number of the output images) of noisy scattered radiation images of low quality (LQ) are also simulated. These LQ scattered radiation images are simulated with a smaller amount of photons compared to the HQ scattered radiation images. Therefore the additional simulation time that is needed for estimation of the LQ scattered radiation images is negligible. These LQ scattered radiation images may be used in a different way, in order for example also to train a neural network based only on the LQ scattered radiation images and a selection of output images (this is not claimed here).

LQ scattered radiation images in this case are the sole input for the neural network (or the algorithm or the artificial intelligence), that is trained to derive HQ scattered radiation images. The neural network is trained on a few LQ-HQ pairs and then applied directly to (all) LQ scattered radiation images. In this way the neural network may be interpreted either as a denoising algorithm or as an algorithm for surface adaptation (comparable for example with the B-spline adaptation, with the difference that it has a data-specific component in the learned AI weights).

In an embodiment there is provision that, for the simulation of the high-quality and low-quality scattered radiation images, an uncorrected 3D image is reconstructed from the plurality of output images and the high-quality and low-quality scattered radiation images are simulated directly on the basis of the uncorrected 3D image.

Thus with the aid of the uncorrected output images, an uncorrected 3D image of the object to be imaged is created. This uncorrected 3D image is the basis for the simulation of the scattered radiation images. As an alternative the simulation could also be undertaken on the basis of the output images themselves, without the intermediate step of the reconstruction of a 3D image. The reconstructed 3D image has the advantage however that further simulated scattered radiation images could be obtained without further effort.

In an embodiment there is provision for the imaging apparatus to be an x-ray apparatus and for example a C-arm device, with which the output images are obtained. The imaging apparatus is thus based on x-ray technology. The imaging modality may thus for example also be configured as an x-ray imaging modality, for example as a digital x-ray imaging device, for example as a C-arm-x-ray imaging modality (i.e. C-arm device). The imaging modality in this case for example includes an x-ray source and also a sensor unit. The sensor unit may for example include a detector array, for example a two-dimensional detector array, of optical detectors, for example photodiodes, that may generate the at least one sensor dataset.

In an embodiment with the C-arm device the simulated scattered radiation images may be evenly distributed with regard to the recording coordinates over a recording region of the C-arm device. If for example in the C-arm device a recording region of 200 degrees is selected, then for example one scattered radiation image may be simulated for every 20 degrees. In this way eleven simulated scattered radiation images would be produced for the ten intervals, including a start and end scattered radiation image. The even distribution may however also be based on another number and is not restricted to ten. As an alternative there may also be a deviation from the even distribution, if it emerges for example that the scattered radiation changes especially greatly in a specific angular range. In this case more simulations may be carried out for example for this region of increased change than in other regions.

In an embodiment there is provision for the recording region of the C-arm device to be over 180 degrees and the number of simulated scattered radiation images to lie below 30 and for example below 20. In this case several hundred output images (for example 500) will typically be obtained over a recording region of 180 degrees. Thus for the training only one scattered radiation image is simulated for example for each 25th output image. Thus the training may be carried out significantly more quickly than in the case in which the training is undertaken with all output images and associated scattered radiation images.

In an embodiment the algorithm or the neural network is synchronized before its training with a physical model. Such a synchronization may be undertaken for example as in the publication US 2021/0330274 A1 described above. With this advance synchronization the training does not have to begin completely at zero. Instead the individual weights of the neural network are already given a meaningful preset, that is oriented to the physical circumstances (for example type of recording region, type of patient, x-ray dose et cetera).

In accordance with an embodiment those images are selected from the plurality of output images that have the same recording coordinates as the simulated low-quality and high-quality scattered radiation images, and the selected output images are likewise used for the training of the algorithm. Thus true projections and associated LQ scattered radiation images are given as additional input in the (intraoperative) training phase to the algorithm or to the AI, that is trained to derive HQ scattered radiation images. In the (intraoperative) inference phase all projections and all associated LQ scattered radiation images are fed into the now trained AI in order to derive all associated HQ scattered radiation images. Overall in this case the (few) selected output images and (few) LQ scattered radiation images are used as input data and the (few) HQ scattered radiation images as output data for the training of the algorithm. Through this the algorithm is trained as well on the specific type of the output images or on their content.

In an embodiment there is provision that over all high-quality scattered radiation images in the simulation an expected value and a standard deviation value are established for each pixel and the expected values and also the standard deviation values are used for the training of the algorithm for machine learning. This means that statistical values such as the expected value and the standard deviation may be used to obtain an additional plausibility check in the application of the algorithm. Thus for example an intraoperative training with HQ standard derivations as additional output data may be provided. On the basis of for example rejection samples the resulting HQ scattered radiation images and standard deviations may be adapted by region so that the LQ scattered radiation images are likely samples from the distribution.

According to an embodiment the simulation is undertaken in each case by a Monte Carlo simulation. In carrying out Monte Carlo simulations the simulation results (for example HQ scattered radiation images) are understood as an approximation to the arithmetic expected value. Therefore each scattered radiation pixel value may be understood as the expected value of this pixel. Moreover the variance or standard deviation for each pixel may be estimated simultaneously. Therefore a probability density function may be formulated for each pixel on the basis of normal distributions (defined via expected value/average value and standard deviation). On the basis of for example rejection sampling, the validity of artificially established distributions (AI-based prediction of average value and standard deviation, i.e. HQ scattered radiation images and standard deviations) may be assessed with the aid of samples taken (i.e. LQ or noisy scattered radiation images).

Thus a method for correction of recordings obtained by (x-ray) radiation by simulation of a low-quality scattered radiation image for each output image, creation of a high-quality scattered radiation image for each output image with the aid of an algorithm trained according to the above method (for example neural network), into which all output images and all low-quality scattered radiation images are entered for this, and correction of each output image by the respective corresponding high-quality scattered radiation images is provided. The neural network trained with few simulated high-quality and low-quality) scattered radiation images is provided in order thereby to estimate corresponding scattered radiation images for all output images, so that all output images may be corrected with the respective scattered radiation images. In order to generate an individual scattered radiation image by the neural network for all output images it is thus only necessary in accordance with the invention to train the neural network with a smaller number of pairs of output images and scattered radiation images. The correction of each output image may be undertaken for example by subtraction of an output image with the corresponding scattered radiation image. If necessary however there may also be further processing of the scattered radiation images, such as a weighting or the like, for the correction.

In the application of the algorithm or neural network for creation of all high-quality scattered radiation images (corresponding to the number of output images) only the low-quality scattered radiation images corresponding to the number of output images are entered as input data into the algorithm, if this is only trained with the low-quality scattered radiation images. Otherwise, if the algorithm has been trained with the low-quality scattered radiation images and the output images, in the application of the algorithm for creation of all high-quality scattered radiation images, both all output images and also the corresponding low-quality scattered radiation images are entered as input data.

According to an embodiment the number of simulated scattered radiation images for training may be automatically increased until such time as a predetermined precision in relation to pixel values in respect of the recording coordinates of neighboring scattered radiation images is reached. Thus, for example, if the pixel values of predetermined pixels of neighboring scattered radiation images fluctuate by more than a predetermined amount, this may be a sign of an insufficiently trained neural network. Therefore in this case the number of the training pairs of output images and scattered radiation images is increased. This increase may be performed successively until the pixel values of individual pixels of neighboring scattered radiation images no longer deviate disproportionately from one another, i.e. the error lies below a predetermined threshold.

In an embodiment a check is made pixel by pixel during the creation of each high-quality scattered radiation image as to whether a corresponding pixel value lies within an interval defined by the respective expected value and the respective standard deviation value, and, if this is not the case, the pixel value is interpolated with pixel values of immediately neighboring pixels. In this way specific distributions may be taken into account and applied individually to pixels. In this way the simulated statistical values, that are also used for training the algorithm, allow reliable high-quality scattered radiation images to be obtained by the algorithm.

In an embodiment there is provision for a corrected 3D image to be reconstructed from the corrected output images. For example the output images of a C-arm sequence have been corrected according to the method presented above, whereby the scattered radiation effects have been reduced in the individual images. These corrected individual images or output images may now be the basis for the reconstruction of a 3D image, in order to obtain a corrected 3D image in which the scattered radiation effects are likewise correspondingly reduced.

Thus, a method for obtaining (x-ray) recordings of an object may also be provided, during which a method as has been described above is carried out. This means that in practice an intraoperative training of the neural network takes place. It is trained while x-ray recordings of the object are being obtained within the framework of an intervention for example. The advantage of the method lies in the fact that a neural network is being trained specifically for a male or female patient or a recording and thus a very accurate correction may be achieved. Until now neural networks have been trained based on a large dataset, in the hope of achieving a generalization to unseen data. No intraoperative simulations are then necessary, but often the results are not optimal for individual male or female patients.

Embodiments provide an imaging system with an imaging apparatus and an image processing apparatus, that is configured to carry out one of the methods specified above. For example the imaging system may include a control facility, that is configured to train an algorithm or a neural network for a correction of tasks produced by the imaging apparatus. The imaging apparatus may be configured here to record a plurality of output images with various recording coordinates. The imaging apparatus may be configured in each case to obtain a number of simulated high-quality and low-quality scattered radiation images that is less than the plurality of output images by a scattered radiation model from the plurality of output images, wherein each pair of simulated scattered radiation images is assigned (at least) one respective recording coordinate. The imaging apparatus or its control facility may for example be configured to select those of the plurality of output images of which the respective recording coordinates correspond to those of the simulated scattered radiation images, and to train the neural network with the selected output images as input data and the simulated scattered radiation images as output data.

For application cases or application situations that may emerge in the method and that are not described explicitly here, there may be provision that, in accordance with the method, an error message and/or a request for input of a user acknowledgement is output and/or that a default setting and/or a predefined initial state is set.

Further forms of embodiment of the imaging system follow on from the various forms of embodiment and vice versa. For example the imaging system may be configured to carry out a method according to the improved training or correction concept.

In an embodiment, a computer program (product) with instructions is also specified. When the instructions are executed by an imaging system according to the improved concept, for example by a control or processing unit of the imaging system, the instructions cause the imaging system to carry out a method in accordance with the concept described herein.

The computer program product may be configured in this case as a computer program product with the instructions. The computer program product may also be configured as a computer-readable storage medium or electronically readable data medium, that stores a computer program product with the instructions.

The features and combinations of features given here in the description as well as the features and combinations of features given below in the description of the figures and/or in the figures alone are able to be used not only in the respective specified combination but also in other combinations without departing from the framework of the invention.

DETAILED DESCRIPTION

Figure 1:
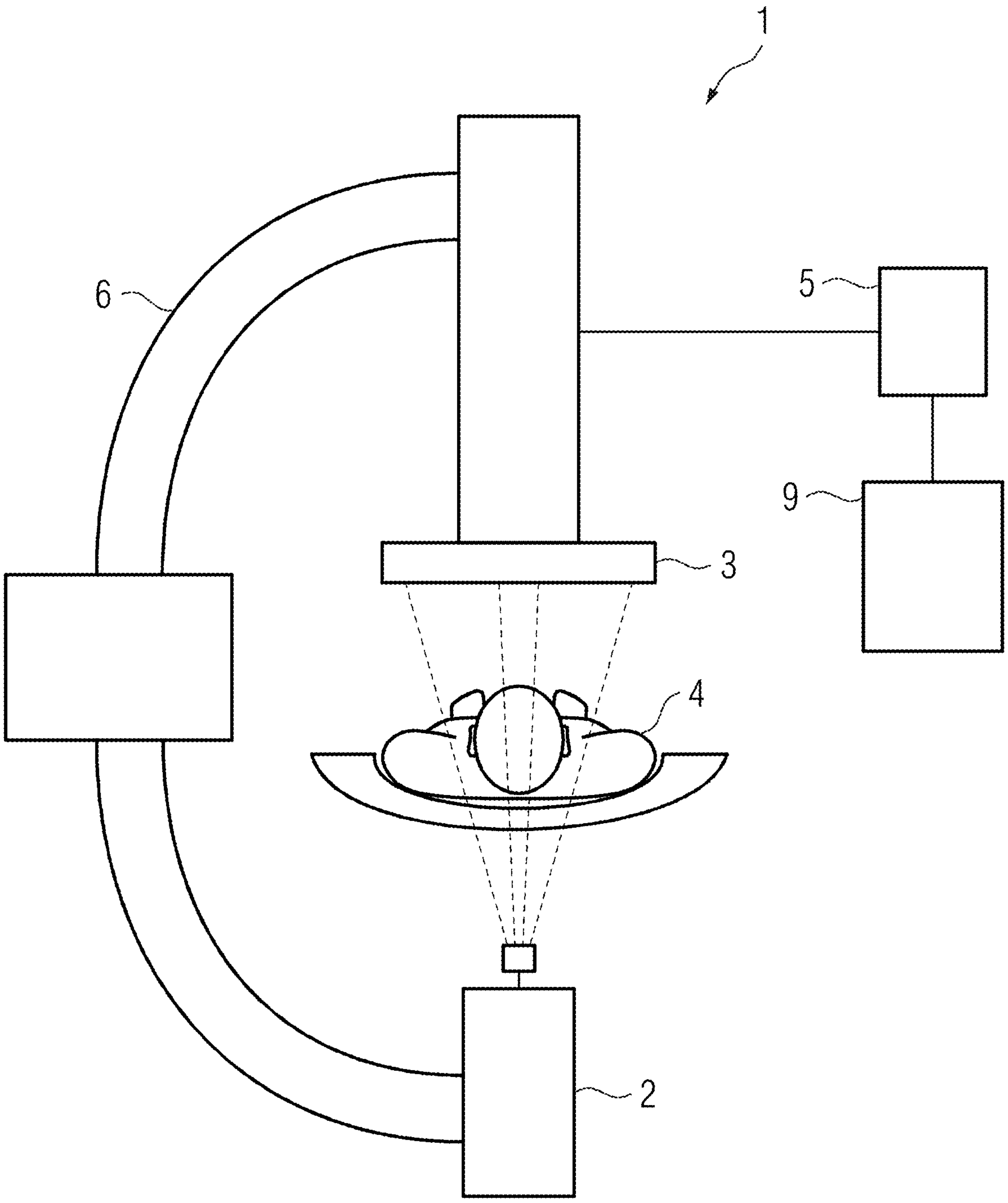
FIG. 1 depicts a schematic diagram of an embodiment of an imaging apparatus.

Shown schematically in FIG. 1 is a form of embodiment of an imaging system 1 that is configured for example as an x-ray imaging system. Shown in the example of FIG. 1 is a construction of the x-ray imaging system or device according to the principle of a C-arm device with a rotatable and movable C-arm 6 that may be turned and moved accordingly in order to image an object 4 to be imaged from different directions, i.e. at various recording angles. An imaging apparatus 1 may however also be constructed in different ways. For example the improved concept is not basically restricted to x-ray-based imaging methods.

The imaging apparatus 1 of FIG. 1 thus for example includes an x-ray source 2, that is configured to generate x-ray radiation and to emit it in the direction of the object 4. A sensor 3 of the imaging apparatus 1, that for example contains a detector array made of photodiodes, is arranged on an opposite side of the object 4 to the x-ray source 2 in order to be able to detect x-ray quanta penetrating the object 4. The sensor 3 may then transfer the corresponding detector signals for example to a control or processing unit 5 of the imaging system 1 for further processing. The components 2 to 6 represent an imaging apparatus that may pass its images on to an image processing apparatus 9. This may make any corrections to the recorded images.

The imaging system 1 may be configured for example for carrying out a rotation angiography method, for example based on the principle of subtraction angiography. In this case the processing unit 5 may for example create a plurality of two-dimensional projections (also called output images here) from various angles and the processing unit 5 may, where necessary, compute a three-dimensional reconstruction therefrom.

The way in which the imaging system 1 functions will be explained in greater detail below with reference to various forms of embodiment of a training and/or correction method, for example with reference to FIGS. 2 to 7.

The three embodiments depicted in conjunction with FIGS. 2 to 7 may each be divided into two major substeps: A training method and the actual correction method.

Overall they represent neural scatter interpolations (NSI). They use the advantages of deep learning and simulation techniques for example. Although it is generally known that deep learning models perform above-averagely in the training cohorts, this effect is still only rarely used in a targeted manner. NSI may be realized as a purely interventional technique that does not depend on prior information.

The two major steps in the embodiment in accordance with FIGS. 2 and 3 will be explained in more detail below. In the first step in accordance with FIG. 2 a plurality of output images 10 is recorded by the imaging apparatus 2 to 6. Each output image 10 is recorded for example by a C-arm from a different angle. In the present example each output image 10 represents an x-ray recording of a chest cavity. Each individual output image 10 is hallmarked by a primary intensity Ip of the primary (x-ray) radiation and a secondary intensity Is of the secondary (x-ray) radiation. In each individual output image 10 the two intensities Ip and Is are first of all overlaid (Ip+Is). The object is to free each individual output image 10 from the secondary intensity Is. To do this, in accordance with FIG. 2, a neural network 11 is to be trained, in order to finally use it in accordance with FIG. 3 for a correction of the stack of output images 10.

Figure 2:
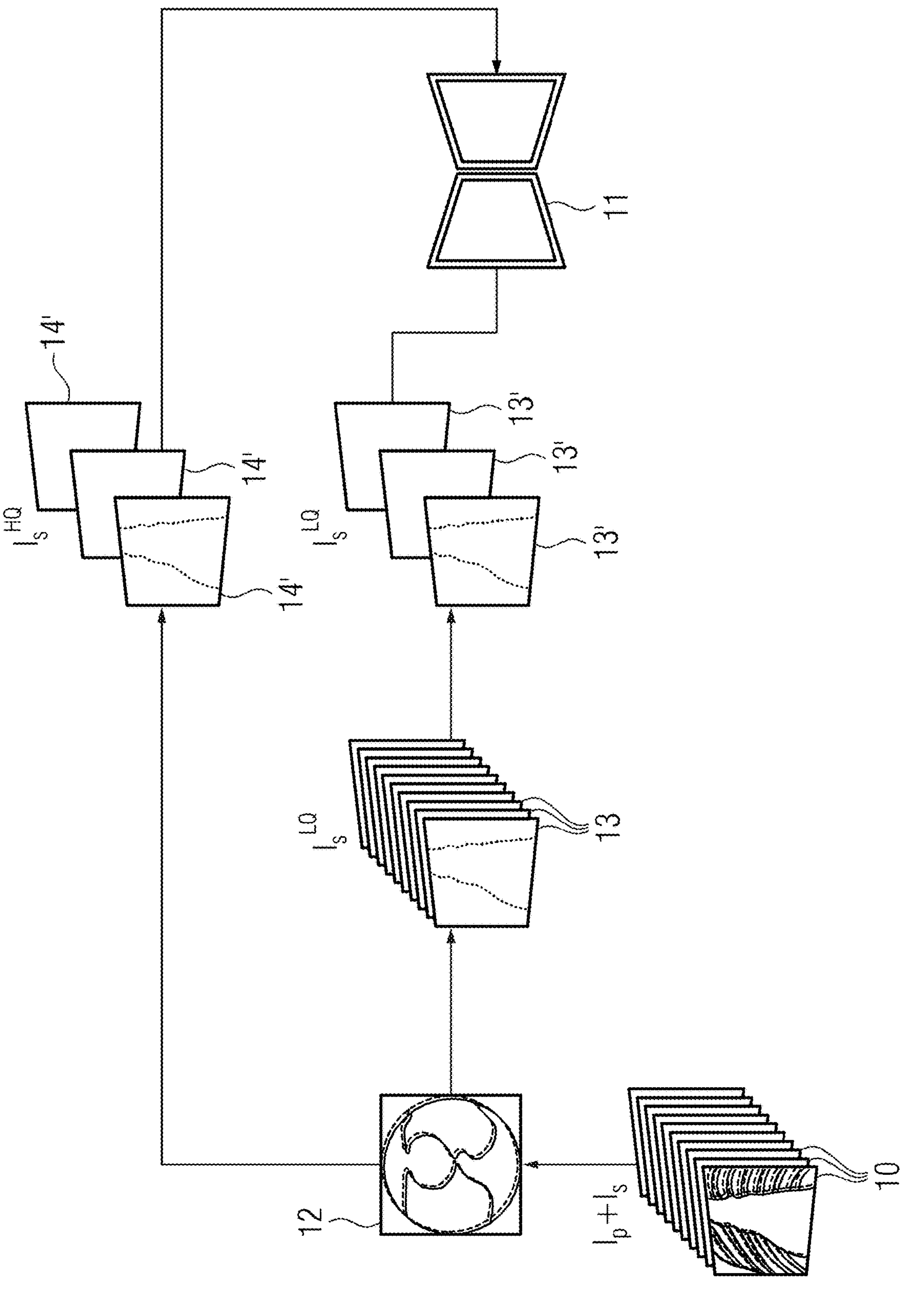
FIG. 2 depicts a schematic visualization of an embodiment of an training method.

In the first step (training phase) in accordance with FIG. 2 a first, uncorrected reconstruction 12 (3D image) is computed using the entire stack of projections, i.e. output images 10. On the basis of this uncorrected reconstruction 12 a low-quality scattered radiation image 13 (intensity $$I_s^{LQ})$$

with the recording coordinates of the output images 10 may be simulated on the basis of a first photon number, that output images are produced (evenly) along the recording trajectory (for example CBCT trajectory). For example a selection is made for each tenth recording setting from the set of low-quality scattered radiation images 13, that leads to few selected low-quality scattered radiation images 13'. Furthermore a number of selected high-quality scattered radiation images 14' (intensity $$I_s^{HQ})$$

with the same recording coordinates as the selected low-quality scattered radiation images 13' is simulated here on the basis of the uncorrected reconstruction 12 based on a second photon number, that is larger than the first photon number. The number of the selected high-quality scattered radiation images 14' is thus also smaller (by at least one order of magnitude for example) than the overall number of the output images 10. The simulation is undertaken with the aid of a scatter model for example on the basis of the uncorrected reconstruction 12 or the stack of output images 10.

Experiments have shown that for example ten to 20 scatter simulations, i.e. simulated selected scattered radiation images 13' or 14', are sufficient to cover the angular range of a short scan (200 degrees).

The selected scattered radiation images 13', 14' are simulated for specific recording coordinates (for example recording angles) of the recording trajectory. Preferably the recording coordinates or corresponding simulated selected scattered radiation images 13', 14' are evenly distributed over the recording trajectory. The number of simulated selected low-quality scattered radiation images 13' and the number of simulated selected high-quality scattered radiation images 14' is the same.

The algorithm 11 for machine learning (for example the neural network) is trained with the aid of the simulations, i.e. the simulated, selected low-quality scattered radiation images 13' and the corresponding selected high-quality scattered radiation images 14'. The selected low-quality scattered radiation images 13' serve as the so-called input layer and the selected high-quality scattered radiation images 14' as the so-called output layer for the training.

The architecture of the neural network or of the algorithm 11 is freely selectable, however a combination with a physically informed neural network, as disclosed in the publication US 2021/0330274 A1, is recommended.

The training of the neural network 11 may be a purely interventional or intraoperative technique and does not depend on prior information.

Figure 3:
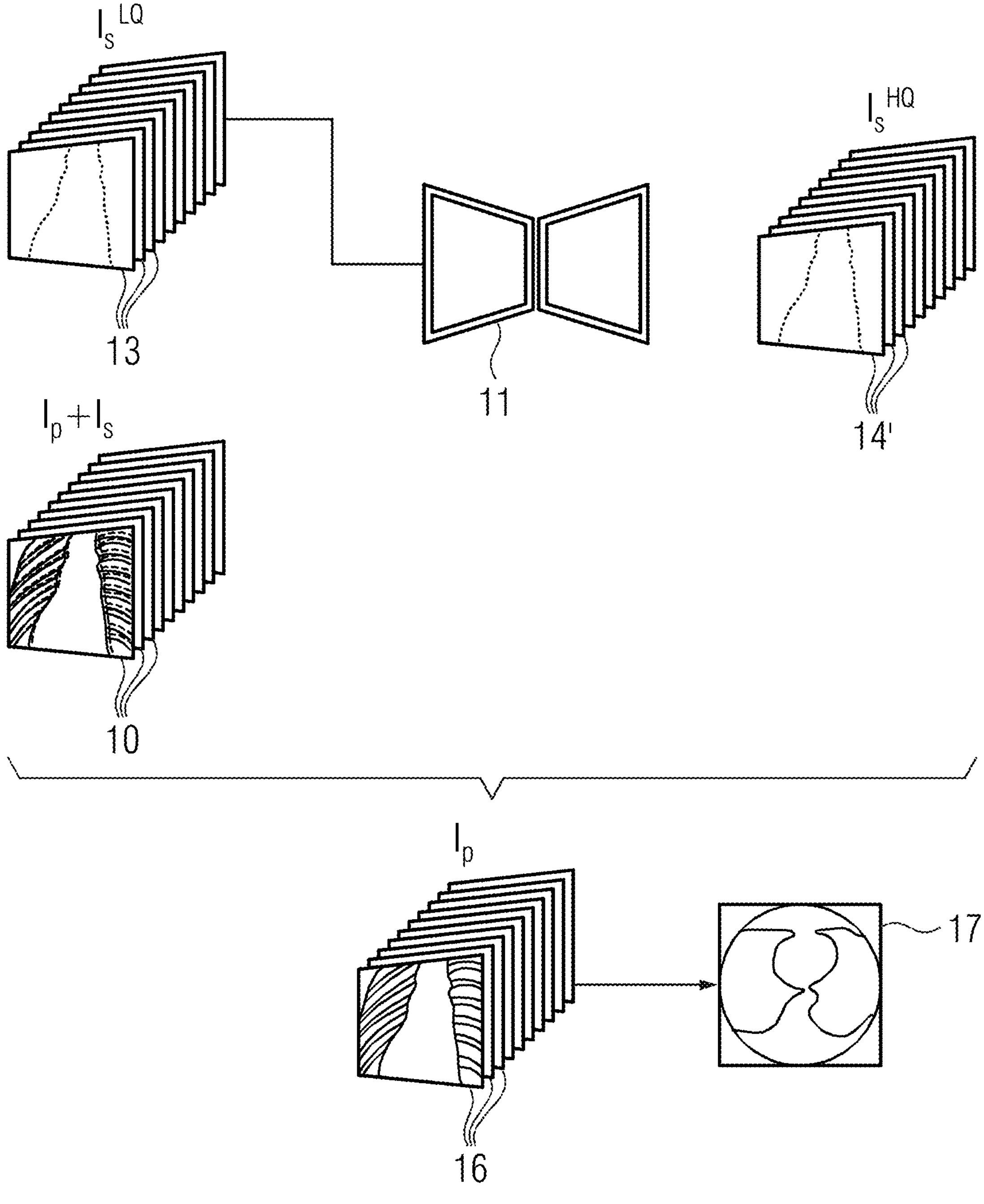
FIG. 3 depicts a visualization of a correction method according to an embodiment.

In a second step (application phase) in accordance with FIG. 3, a high-quality scattered radiation image 14 is computed for all low-quality scattered radiation images 13 (obtained in the first step) with the aid of the trained neural network 11. While the output images 10 possess the intensity Ip+Is, the computed high-quality scattered radiation images have the simulated intensity or intensity distribution $$I_s^{HQ},$$

that corresponds to the denoised scattered radiation intensity Is. They thus represent the intensity distribution of the secondary radiation at the respective recording coordinate. The scatter distributions of the individual high-quality scattered radiation images 14 may be used directly for correcting all recorded projections or output images 10. The correction of the original output images 10 with the same number of high-quality scattered radiation images 14 produces corrected output images 16 once again in the same number. In the correction for example of an output image 10 the corresponding high-quality scattered radiation image 14 is subtracted in order to obtain a respective corrected output image 16. In relation to the intensity distribution the correction may be expressed as follows: (Ip+Is)−Is=Ip. Thus each corrected output image 16 is freed from the respective specific scattered radiation. A corrected 3D image 17 may now be reconstructed from the corrected output images 16, that corresponds in its number to the original output images. This corrected 3D image 17 is free from scatter errors.

Figure 4:
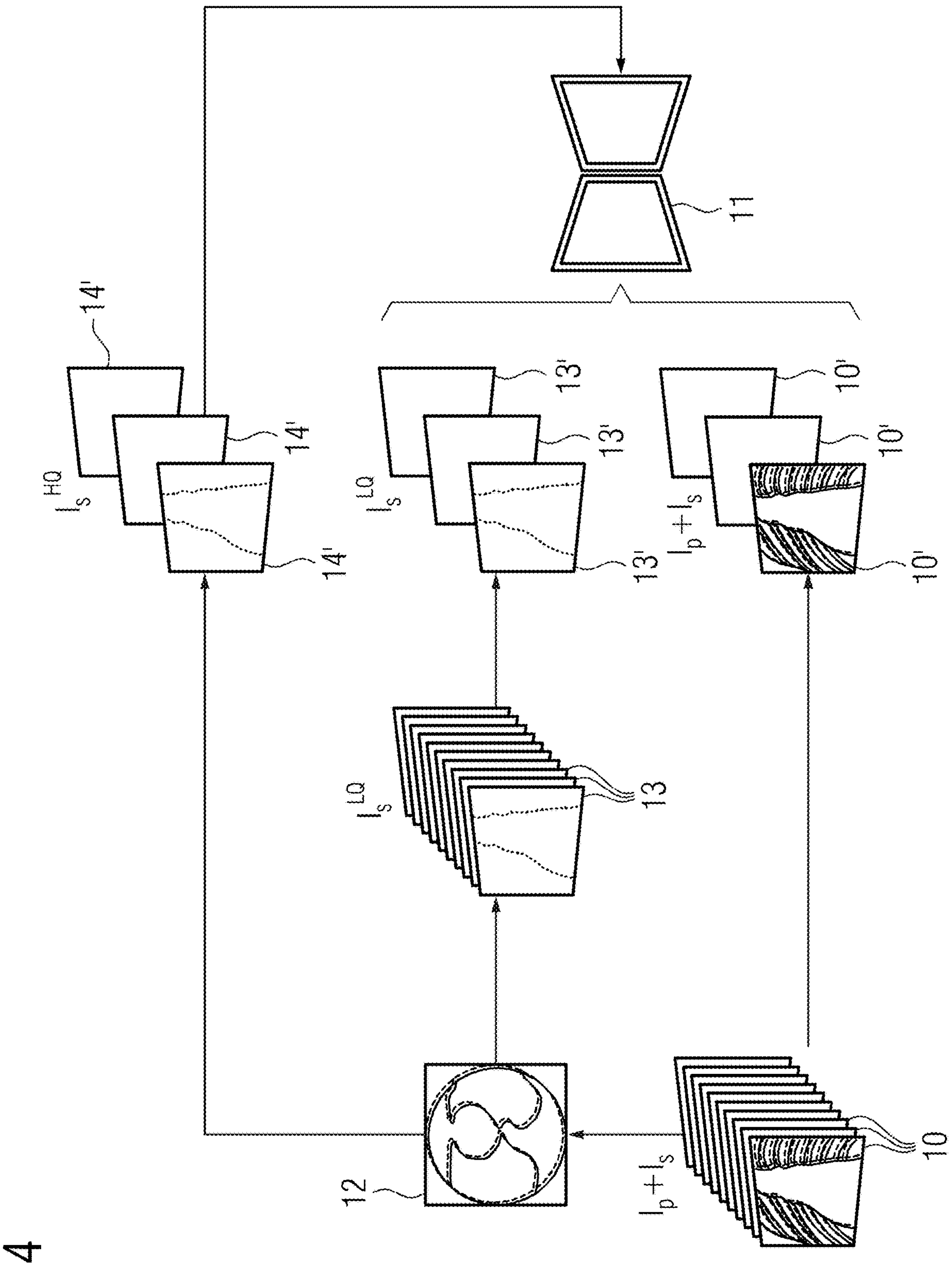
FIG. 4 depicts a schematic visualization of another embodiment of a training method.

FIG. 4 depicts a further embodiment for training the algorithm 11 for machine learning. The training corresponds to that of the embodiment of FIG. 2. Therefore the reader is referred for the description of this embodiment to the description of FIG. 2. In addition a set of selected output images 10' is selected from the total amount of the output images 10. The selected output images 10' have the same recording coordinates as the selected low-quality scattered radiation images 13' and the selected high-quality scattered radiation images 14'. The algorithm 11 is additionally provided here for training with the selected output images 10' as well as the selected low-quality scattered radiation images 13' as input data. As before, the selected high-quality scattered radiation images 14' represent the output data for training the algorithm 11.

Figure 5:
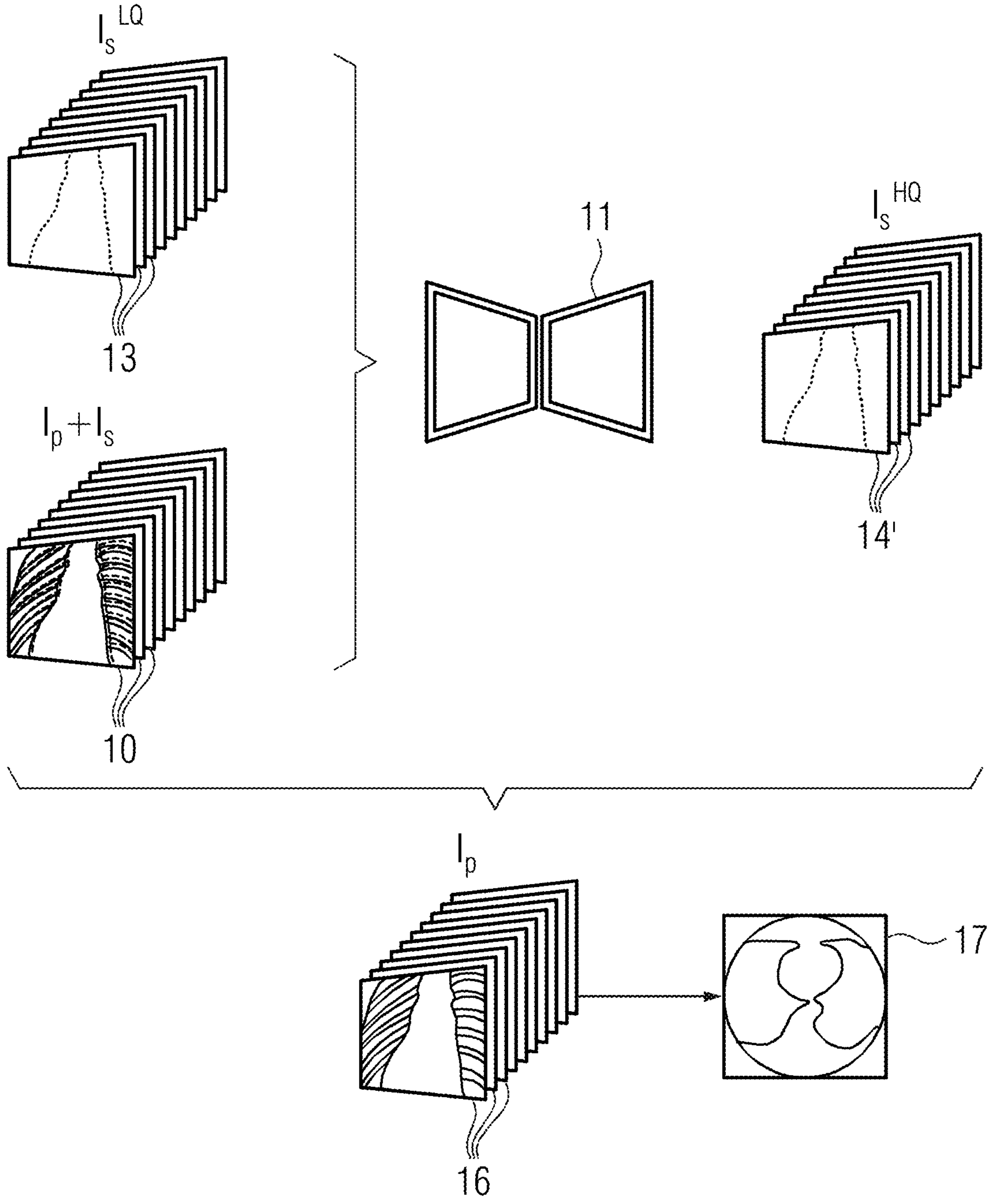
FIG. 5 depicts a visualization of another correction method according to an embodiment.

The algorithm 11 trained in accordance with the embodiment of FIG. 4 may be applied according to the example from FIG. 5. The algorithm is applied here in a similar way to the example from FIG. 3. Here however, along with all low-quality scattered radiation images 13, all output images 10 are also entered into the algorithm 11 as input data in order to obtain all high-quality scattered radiation images 14. For the correction, here too the high-quality scattered radiation images 14 are now subtracted from the output images 10, that have actually already been made available for input to the algorithm 11 in order to obtain the corrected output images 16. The latter are then again the basis for the reconstruction of the 3D image 17.

Figure 6:
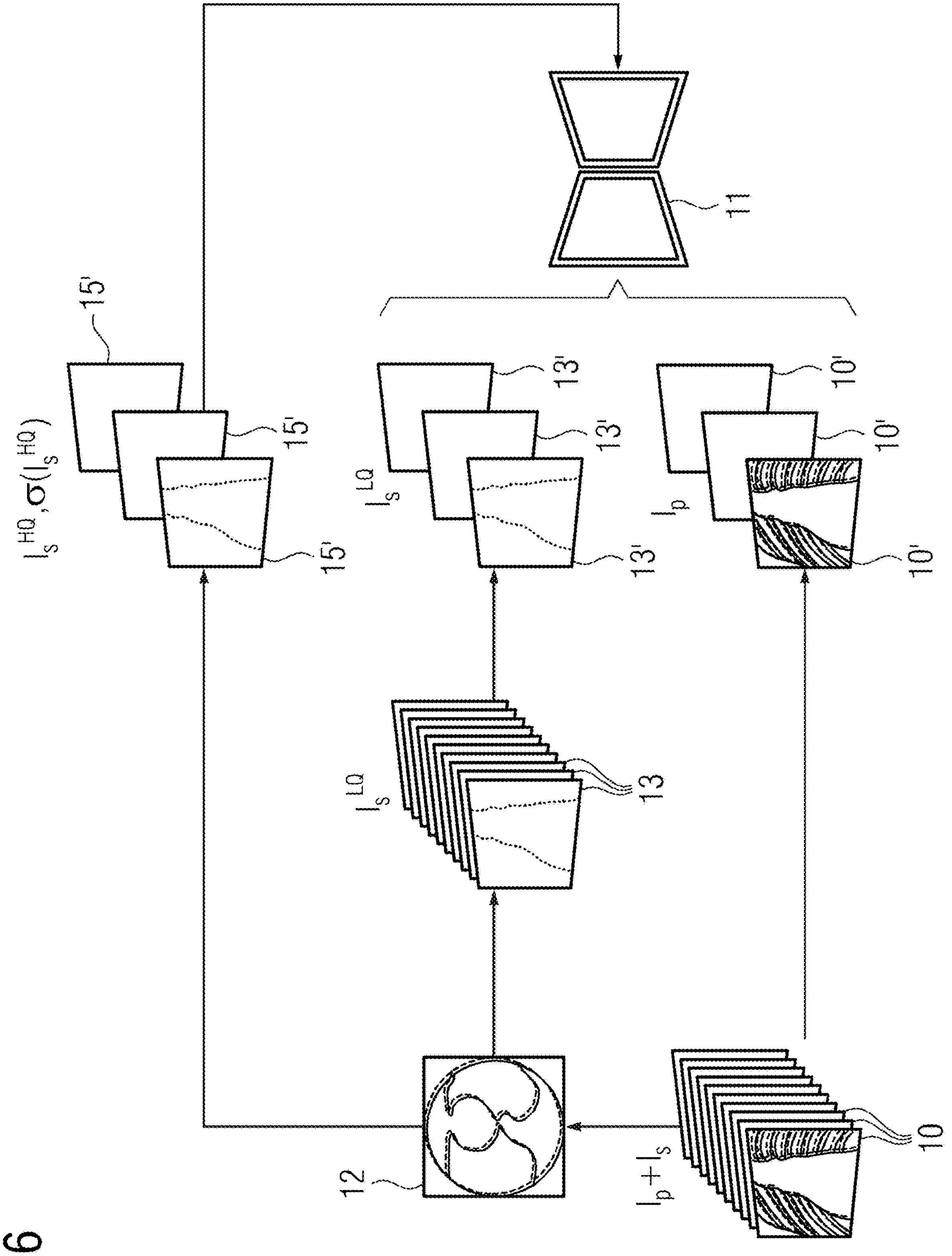
FIG. 6 depicts a schematic visualization of an embodiment of a training method.

A further embodiment of the training of the algorithm 11 is shown in FIG. 6. It is based on the embodiment from FIG. 4. The difference merely lies in the fact that, in the simulation of the selected high-quality scattered radiation images, the standard deviations $$\sigma(I_s^{HQ})$$

are also computed pixel by pixel. Thus selected, expanded high-quality scattered radiation images 15' are produced, that are based both on the high-quality scattered radiation intensities $$I_s^{HQ}$$

and also on the associated standard deviations $$\sigma(I_s^{HQ}).$$

These selected, expanded high-quality scattered radiation images 15' are used in this example as output data during training of the algorithm 11. The input data during training corresponds to that of the example from FIG. 4.

Figure 7:
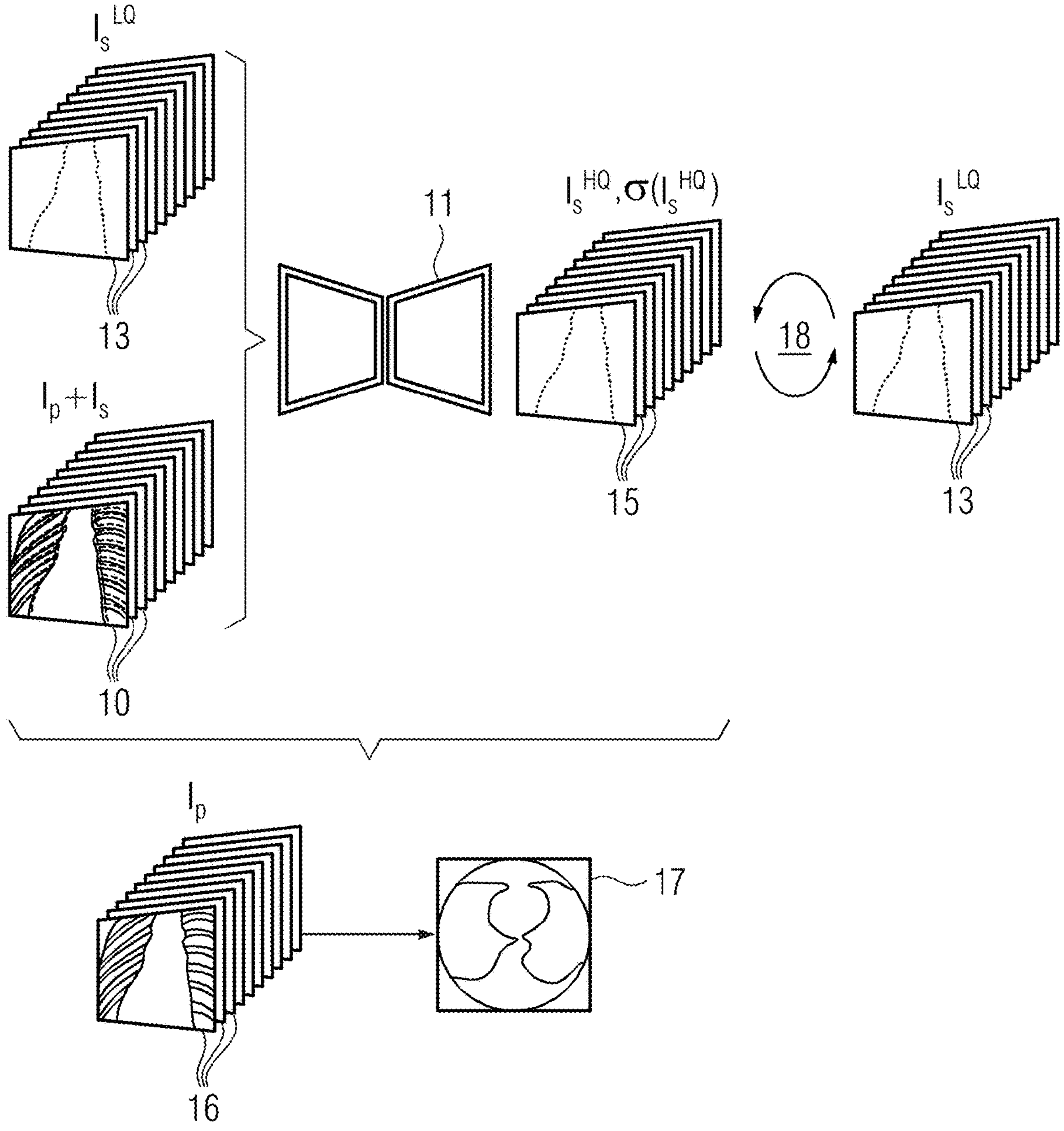
FIG. 7 depicts a visualization of a correction method according to an embodiment.

The application of the algorithm 11 trained in this way is shown by way of example in FIG. 7. It is based on the application in accordance with the example from FIG. 5, which is why the reader is referred to the description given there. By contrast with the example from FIG. 5, in the example from FIG. 7 a complete set of expanded high-quality scattered radiation images 15 is computed with the aid of the trained algorithm 11 from the low-quality scattered radiation images 14 and the output images 10. The number of these expanded high-quality scattered radiation images 15 corresponds to the number of the low-quality scattered radiation images 13 and the number of the output images 10. All expanded high-quality scattered radiation images 15, as well as the computed intensities $$I_s^{HQ}$$

(arithmetic averages) also include the standard deviations $$\sigma(I_s^{HQ}).$$

This application too may be performed intraoperatively.

In a post-processing or iterative refinement step 18 the artificial high-quality scattered radiation images are adapted iteratively with the aid of the standard deviations so that the actually simulated low-quality scattered radiation images 13 are meaningful samples from these normal distributions.

The embodiment in accordance with FIG. 2 may also be implemented as pretrained AI, that is trained on any kind of scatter simulation. The assignment of LQ scatters to HQ scatters is by nature simpler than the assignment of real projection images to HQ scatters, since it only involves a denoising or surface adaptation method, that is based on incomplete samples.

In an expanded embodiment there may be provision for the neural network 11 to be pretrained or initialized for example with a physical model. This has the advantage that the neural network initialized in this way may already be employed before the intraoperative training in accordance with FIG. 2.

According to another embodiment, an expected precision of the pixel values of the simulated scattered radiation images 13 may be defined. If this precision cannot be achieved during the intraoperative training, additional simulations may be carried out until it is achieved. This means that number of the simulated scattered radiation images 13 is increased automatically for example until the desired precision is reached. The inventive approach makes it possible for the online simulation, a training, and the productive use (inference) of the neural network to be combined within a single intervention method. This leads to the following advantages: On the one hand the computing complexity may be reduced by a factor of up to 50 by comparison with purely simulation-driven approaches. Since the training of the network is only carried out with around 10 datasets for example, the run time for this is negligible, as is the effort involved in applying it.

On the other hand the neural scatter interpolation (NSI) is by nature robust by comparison with pure deep learning methods. It is inherently ensured that no data occurs outside the distribution. Moreover the expected precision may already be monitored during the training of the network on the basis of the training data or possible additional validation data. If the expected precision does not fulfill a defined quality criterion, additional simulations may be carried out until the quality criterion is fulfilled.

Thus, in an advantageous way a method may be provided that includes scatter estimations of low quality in the training and/or inference process for AI-based scatter estimation. For example scatter estimations of low quality as known samples from an unknown distribution may be used. Thus robust and rapid estimations of scatters are made possible since scatter images of low quality serve as guidelines in the training and inference process.

It is to be understood that the elements and features recited in the appended claims may be combined in different ways to produce new claims that likewise fall within the scope of the present embodiments. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present embodiments have been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for training an algorithm for machine learning for a correction of recordings obtained by an imaging apparatus, the method comprising:

recording, by the imaging apparatus, a plurality of output images with various recording coordinates;

simulating a number of first scattered radiation images that is less than the plurality of output images, by a scatter model from the plurality of output images, wherein the simulation is undertaken with a first number of photons, and wherein each first scattered radiation image is assigned a respective recording coordinate;

simulating the number or a higher number of second scattered radiation images by the scatter model from the plurality of output images, wherein the simulation of second scattered radiation images is undertaken with a second number of photons reduced by comparison with the first number, which is reduced by at least an order of magnitude, and wherein respective recording coordinates of the second scattered radiation images correspond to those of the first scattered radiation images; and training the algorithm for machine learning with the second scattered radiation images as input data and the first scattered radiation images as output data.

2. The method of claim 1, wherein for the simulation of the first scattered radiation images and the second scattered radiation images an uncorrected 3D image is reconstructed from the plurality of the output images, and the first scattered radiation images and the second scattered radiation images are simulated directly based on the uncorrected 3D image.

3. The method of claim 1, wherein the imaging apparatus is an x-ray apparatus.

4. The method of claim 1, wherein images are selected from the plurality of output images that have the same recording coordinates as the simulated second scattered radiation images and the first scattered radiation images, wherein the selected images are used for the training of the algorithm.

5. The method of claim 1, wherein an expected value and a standard deviation value are established across all first scattered radiation images in the simulation for each pixel, and the expected values and the standard deviation values are used for the training of the algorithm for machine learning.

6. The method of claim 1, wherein simulating the first scattered radiation images and/or the second scattered radiation images is performed using a Monte Carlo simulation.

7. An imaging system comprising:

an imaging apparatus configured to record a plurality of output images with various recording coordinates; and an image processing apparatus configured to:

simulate a number of first scattered radiation images that is less than the plurality of output images, by a scatter model from the plurality of output images, wherein the simulation is undertaken with a first number of photons, and wherein each first scattered radiation image is assigned a respective recording coordinate;

simulate the number or a higher number of second scattered radiation images by the scatter model from the plurality of output images, wherein the simulation of second scattered radiation images is undertaken with a second number of photons reduced by comparison with the first number, which is reduced by at least an order of magnitude, and wherein respective recording coordinates of the second scattered radiation images correspond to those of the first scattered radiation images; and train an algorithm for machine learning with the second scattered radiation images as input data and the first scattered radiation images as output data.

8. A non-transitory computer implemented storage medium, including machine-readable instructions stored therein for training an algorithm for machine learning for a correction of recordings obtained by an imaging apparatus, the machine-readable instructions when executed by at least one processor, cause the processor to:

record a plurality of output images with various recording coordinates;

simulate a number of first scattered radiation images that is less than the plurality of output images, by a scatter model from the plurality of output images, wherein the simulation is undertaken with a first number of photons, and wherein each first scattered radiation image is assigned a respective recording coordinate;

simulate the number or a higher number of second scattered radiation images by the scatter model from the plurality of output images, wherein the simulation of second scattered radiation images is undertaken with a second number of photons reduced by comparison with the first number, which is reduced by at least an order of magnitude, and wherein respective recording coordinates of the second scattered radiation images correspond to those of the first scattered radiation images; and train the algorithm for machine learning with the second scattered radiation images as input data and the first scattered radiation images as output data.

* * * * *